United States Patent
Kunugi et al.

(10) Patent No.: US 10,043,979 B2
(45) Date of Patent: Aug. 7, 2018

(54) ORGANIC SEMICONDUCTOR DEVICE THAT USES CHRYSENE COMPOUND

(71) Applicant: USHIO CHEMIX KABUSHIKI KAISHA, Omaezaki-Shi (JP)

(72) Inventors: Yoshihito Kunugi, Hiratsuka (JP); Kazuo Okamoto, Omaezaki (JP); Hiroyuki Otsuki, Omaezaki (JP)

(73) Assignee: USHIO CHEMIX CORPORATION, Shizuoka-Ken (JP)

( * ) Notice: Subject to any disclaimer, the term of this patent is extended or adjusted under 35 U.S.C. 154(b) by 131 days.

(21) Appl. No.: 14/471,672

(22) Filed: Aug. 28, 2014

(65) Prior Publication Data

US 2015/0129807 A1    May 14, 2015

(30) Foreign Application Priority Data

Nov. 12, 2013    (JP) ................. 2013-233601

(51) Int. Cl.
| | |
|---|---|
| H01L 51/00 | (2006.01) |
| C07C 13/66 | (2006.01) |
| C09K 19/32 | (2006.01) |
| C07C 13/62 | (2006.01) |
| H01L 51/05 | (2006.01) |

(52) U.S. Cl.
CPC .......... *H01L 51/0054* (2013.01); *C07C 13/62* (2013.01); *C09K 19/322* (2013.01); *C07C 2603/48* (2017.05); *C09K 2211/1011* (2013.01); *H01L 51/0545* (2013.01); *H01L 51/0558* (2013.01)

(58) Field of Classification Search
None
See application file for complete search history.

(56) References Cited

U.S. PATENT DOCUMENTS

2011/0180790 A1*    7/2011 Nakano ................. C07C 15/38
257/40

FOREIGN PATENT DOCUMENTS

| JP | 2010-118415 A | 5/2010 |
|---|---|---|
| JP | 2013-152961 A | 8/2013 |
| WO | 2008/059816 A1 | 5/2008 |

OTHER PUBLICATIONS

Kunugi et al., "Single Crystal Organic Field-Effect Transistors Based on 2,8-Diphenyl and Dinaphthyl Chrsenes", Journal of Photopolymer Science and Technology, vol. 24, No. 3 (2011) pp. 345-348.

* cited by examiner

*Primary Examiner* — Katie L Hammer
(74) *Attorney, Agent, or Firm* — Bacon & Thomas, PLLC

(57) ABSTRACT

An organic semiconductor material having a chrysene skeleton by limiting a compound having particular transistor performance. The chrysene compound is represented by the following chemical formula:

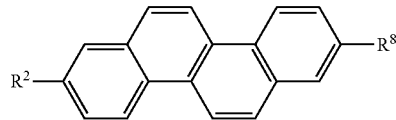

In the chemical formula, R2 and R8 are not the same functional group, and independently includes at least one of a hydrogen atom, a substituted or non-substituted aryl group, a substituted or non-substituted heterocyclic group and a substituted or non-substituted alkyl group.

10 Claims, 3 Drawing Sheets

FIG. 3

ORGANIC SEMICONDUCTOR DEVICE THAT USES CHRYSENE COMPOUND

FIELD OF THE INVENTION

Present invention relates to compounds particularly excellent in a transistor performance among compounds having a chrysene skeleton, and organic semiconductor devices that use the compound.

BACKGROUND

The present inventors found that a compound having a chrysene skeleton is a novel organic semiconductor material that shows, while overcoming instability of pentacene, a high performance also as an organic transistor, applied a patent request that has a name of invention of "Semiconductor Material that uses Organic Compound having Chrysene Skeleton", after procedures of amendments and the like, the patent request was admitted, and a patent right was acquired (Patent Document 1: hereinafter, this may be called a first patent application).

Then, a research of an organic compound having a chrysene skeleton (hereinafter, referred to as chrysene compound) was forwarded, and it was clarified that high transistor characteristics can be obtained by experimentally producing a transistor device with a single crystal of particular chrysene compound (Non-patent Document 1). Further, it was found that an organic semiconductor device excellent in the transistor performance can be obtained not only in single crystal but also in polycrystal by combining an insulator layer of a hydrophobic insulating material containing a halogen atom and a thin film layer of the chrysene compound, and a request for patent was filed (Patent Document 2: hereinafter, this may be referred to as second patent application).

Regarding the first patent application, in the stage of examination, a reason for refusal was shown that Patent Document 3 discloses an organic thin film transistor having a chrysene derivative (compounds 24, 35, 45 and so on: hereinafter these are regarded as compounds of the Patent Document 3). In order to solve this problem, a range of claims was reduced in a limiting range by amendment, and the patent right was allowed as described above.

A second patent application is an invention of narrower concept with the invention described in the initial specification and the like of the first patent application as a broader concept, and the same aryl groups are bisymmetrically added with the chrysene skeleton at a center.

Further, the present inventors advanced a research of the chrysene compound and, not in the chrysene compound in which the same aryl groups are bisymmetrically added with the chrysene skeleton at the center but in the chrysene compound having asymmetric functional groups, a compound particularly excellent in the transistor performance was found, and this is applied as a patent (hereinafter, this is regarded as the present invention).

The present application is also an invention of a narrower concept with the invention described in the initial specification and the like of the first patent application as a broader concept. It goes without saying that when a former application is represented by the broader concept and a latter application is represented by the narrower concept, it is not meant that in the former application, the invention represented by the narrower concept is represented, that is, the present application is understood that it has novelty and so-called inventive step. Now, each of the chrysene compounds of the Patent Document 3 is different from the chrysene compounds of the present application and has bisymmetrical functional groups with the chrysene skeleton as a center.

[Patent Document 1] Japanese Patent Application Publication No. 2008-289317 (that was published as JP 2010-118415A and then allowed as JP5335379B)

[Patent Document 2] Japanese Patent Application Publication No. 2012-011588 (that was published as JP2013-152961A) [Patent Document 3] WO2008/059816A1

[Non-patent Document 1] "Single Crystal Organic Field-effect Transistors Based on 2,8-Diphenyl and Dinaphthyl Chrysenes" by Yoshihito Kunugi, Tatsuya Arai, Norihito Kobayashi, Hiroyuki Otsuki, Toru Nishinaga, and Kazuo Okamoto, "Journal of Photopolymer Science and Technology" Vol. 24, No. 3 (2011) pp 345-348.

SUMMARY OF THE INVENTION

The problem to be solved by the present invention is to limit compounds particularly excellent in the transistor performance among organic semiconductor compounds having a chrysene skeleton and to utilize these compounds.

That is, a first invention is an organic semiconductor material having a chrysene skeleton shown by the following chemical formula [CF1].

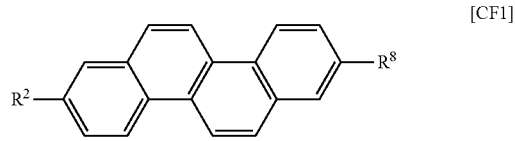

[CF1]

In chemical formula [CF1], R2, R8 each is not the same functional group, but independently represents a hydrogen atom, an alkyl group having 1 to 30 carbon atoms, an aryl group having 5 to 60 carbon atoms, or a heterocyclic group having 3 to 60 carbon atoms, and each of these may have a substituent group.

The alkyl group includes a straight chain, a branched chain and a cyclic alkyl group, and may be any one of a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, a 2-ethylhexyl group, an n-nonyl group, an n-decyl group, a 2-propylheptyl group, an n-undecyl group, an n-dodecyl group, a 2-butyloctyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-henicosane group, an n-docosane group, an n-tricosane group, an n-tetracosane group, an n-pentacosane group, an n-hexacosane group, an n-heptacosane group, an n-octacosane group, an n-nonacosane group, an n-triacontane group, a cyclopentyl group, a cyclohexyl group, a cycloheptyl group, a cyclooctyl group, and an adamantine group, and each thereof may have a substituent group.

The aryl group is any one of a phenyl group, a naphthyl group, an anthryl group, a phenanthryl group, a biphenyl group, chrysene, and tetracene, and each of these groups may have a substituent group.

The heterocyclic group is any one of pyridine, pyrazine, quinoline, naphthyridine, quinoxaline, phenazine, diazaanthracene, pyrroloquinoline, pyrimidoquinazoline, pyrazinoquinoxaline, phenanthroline, carbazole, thiophene, dibenzothiophene, [1]benzothieno[3,2-b]benzothiophene, dinaphto[2,3-b:2',3'-f]thieno[3,2-b]thienothiophene, thienothiophene, dithienothiophene, furan, benzofuran, dibenzofuran, thiazole, benzothiazole, dithiaindacene, dithiaindinoindene, dibenzoselenophene, diselenaindacene, diselenaindenoindene, and dibenzosilole, and each of these groups may have a substituent group.

Examples of the substituent groups include a fluorine atom, a chlorine atom, a bromine atom, an iodine atom, an alkyl group, an alkenyl group, an alkynyl group, an alkoxy group, an aryl group, and a heterocyclic group. The alkenyl group includes an ethenyl group and an ethenyl group having the substituent group. The alkyl group, aryl group, and heterocyclic group are the same as those described above. The alkynyl group includes an ethynyl group and an ethynyl group having the substituent group. The alkoxy group is a compound represented by —OR, O represents an oxygen atom, and R represents the alkyl group.

Subsequently, a second invention is the organic semiconductor material of the first invention, which has a chrysene skeleton represented by the following chemical formula [CF2].

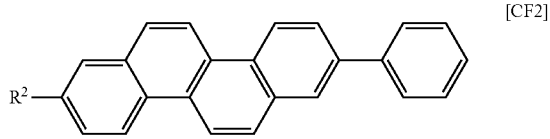

[CF2]

In the chemical formula [CF 2], R2 represents a hydrogen atom, an alkyl group having 1 to 30 carbon atoms, an aryl group having 5 to 60 carbon atoms, and each of these groups may have a substituent group. The substituent group is the same as that described above.

The chemical formula [CF 2] is a narrower concept of the chemical formula [CF 1] and represents an organic semiconductor material contained in the chemical formula [CF 1]. The reason why this is regarded as a second invention is because among the organic semiconductor materials of the chemical formula [CF 1], an organic semiconductor material of the chemical formula [CF 2] shows a particular transistor performance, and we intend to protect these materials. Since R2 is not the same functional group, a non-substituted phenyl group is eliminated.

Next, a third invention relates to the organic semiconductor material according to the first invention, which has a chrysene skeleton represented by the following chemical formula [CF 3].

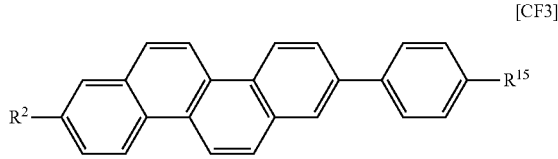

[CF3]

In the chemical formula [CF 3], R2, R15 each independently represents a hydrogen atom, an alkyl group having 1 to 30 carbon atoms, and the alkyl group may have a substituent group. The substituent group is the same as that described above.

Also the chemical formula [CF 3] is the narrower concept of the chemical formula [CF 1] and an organic semiconductor material contained in the chemical formula [CF 1]. The reason why this is regarded as a third invention is due to the same reason as the second invention.

Next, a fourth invention relates to an organic semiconductor device that uses the organic semiconductor material according to any one of the first invention, second invention or third invention, or an organic electronic device that uses any of organic semiconductor materials according to the first invention, second invention or the third invention in a combination of a plurality thereof.

According to the first, second and third inventions, organic semiconductor materials made of many chrysene compounds having different functional group or the like are manufactured. These chrysene compounds can be used singularly or in a combination of a plurality of kinds thereof in the organic semiconductor device. Here, the organic semiconductor device means a semiconductor device that uses the chrysene compound represented by the chemical formula [CF 1], chemical formula [CF 2] and chemical formula [CF 3], and an organic transistor, an organic laser, an organic thin film solar battery, an organic memory and the like can be cited.

When the compound of the present invention is used in these organic electronic devices, purification such as removal of impurities becomes necessary to obtain high purity. The compounds of the present invention can be purified according to a liquid chromatography method, a sublimation method, a zone-melting method, a gel permeation chromatography method, a column chromatography method, a distillation method, a recrystallization method, a thermal washing method or the like.

Further, when the compound of the present invention is used in the organic electronic devices, it is mainly used in a form of a thin film, and, as a thin film preparation method, any of a wet process and a dry process may be used. The compound of the present invention can be adapted to the wet process that has a large industrial merit by dissolving in an organic solvent or the like.

As the organic solvent, known solvents such as dichloromethane, chloroform, chlorobenzene, dichlorobenzene, trichlorobenzene, cyclohexanol, toluene, xylene, mesitylene, nitrobenzene, methyl ethyl ketone, diglyme, and tetrahydrofuran can be used. Further, when the compound of the present invention is dissolved in an organic solvent or the like, a temperature and pressure are not particularly limited, however a temperature when dissolving is preferably 0 to 200° C., and more preferably 10 to 150° C. Further, pressure for dissolving is preferable to be in the range of 0.1 to 100 MPa, and more preferable to be in the range of 0.1 to 10 MPa. Further, in place of the organic solvent, supercritical carbon dioxide or the like can be used.

The wet process indicates a spin coat method, a dip coat method, a bar coat method, a spray coat method, an ink jet method, a screen printing method, a planographic printing method, a relief printing method, an intaglio printing method, or the like, and these well-known methods can be used. Further, the dry process indicates a vacuum depositing method, a sputtering method, a CVD method, a laser deposition method, a molecular beam epitaxial growth method, a vapor phase transporting growth method, and the like, and these known methods can be used.

Usage examples of the organic electronic devices that use the organic semiconductor material of the present invention are shown in FIG. 1 and FIG. 2. In FIG. 1, FIG. 2, usage examples of a field effect transistor (hereinafter, referred to as "FET") are cited. From features of the FET, it is used as a switching element or an amplifying element. Because of, in addition to a low gate current, a planar structure, preparation and integration by a wet process are easy, and a large area can be made possible thereby. Here, although the compound of the present invention is mainly used as a p-type semiconductor, it may function also as an n-type semiconductor by a substituent group or a solvent.

According to the first invention, in organic semiconductor materials of chrysene compound, limited chrysene compounds having excellent transistor performance can be provided, in the second and third inventions, among the limited chrysene compounds, the chrysene compounds having particular transistor performance are limited and can be provided. According to the fourth invention, it can be made possible to manufacture an organic semiconductor device that uses the organic semiconductor material of the chrysene compound.

BRIEF DESCRIPTION OF THE DRAWINGS

Figure 3:
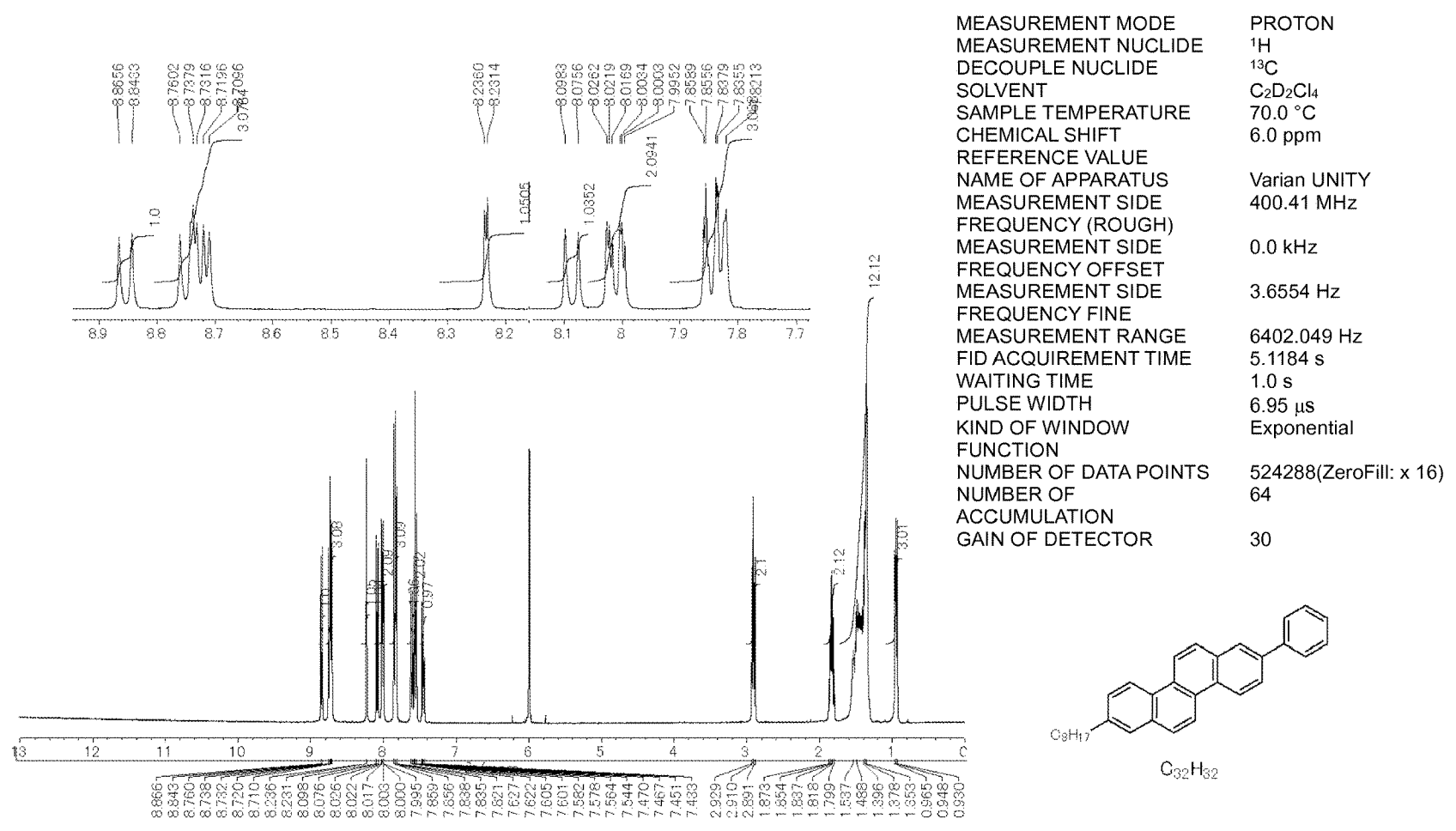

FIG. 3 is a 1H-NMR spectrum diagram of 2-octyl-8-penylchrysene (compound B)

DETAILED DESCRIPTION OF THE INVENTION

Exemplary examples of the present invention will be shown below.

Example 1

A typical synthesis (manufacture) example of an organic semiconductor material having a chrysene skeleton of the first invention will be shown below.

Synthesis (Manufacture) Method of 2-octyl-8-phenylchrysene (Compound B: Hereinafter, Referred to as "P-28CR-8")

Although 2,8-dibromochrysene that is a starting material is not commercially available, since it is described in from paragraphs [0040] to [0044] of the first patent application, the synthesis method thereof is omitted.

Synthesis of Compound A

Under a nitrogen atmosphere, in a 30 mL three-neck flask with a cooling pipe, 1.0 g (2.59 mmol) of 2,8-dibromochrysene, 0.28 g (2.33 mmol) of phenyl boronic acid, 30 mg (0.03 mmol) of tetrakistriphenylphosphine palladium, 0.49 g (4.66 mmol) of sodium carbonate, 15 ml of toluene, and 4 ml of water were added and the mixture was stirred at 80° C. for 16 hours. After the end of the reaction, the mixture was cooled to room temperature, heptane and water were added and crystal was filtrated thereby. The resulted crude product was purified by column chromatography and recrystallization, and a compound A was obtained.

Synthesis of Compound B

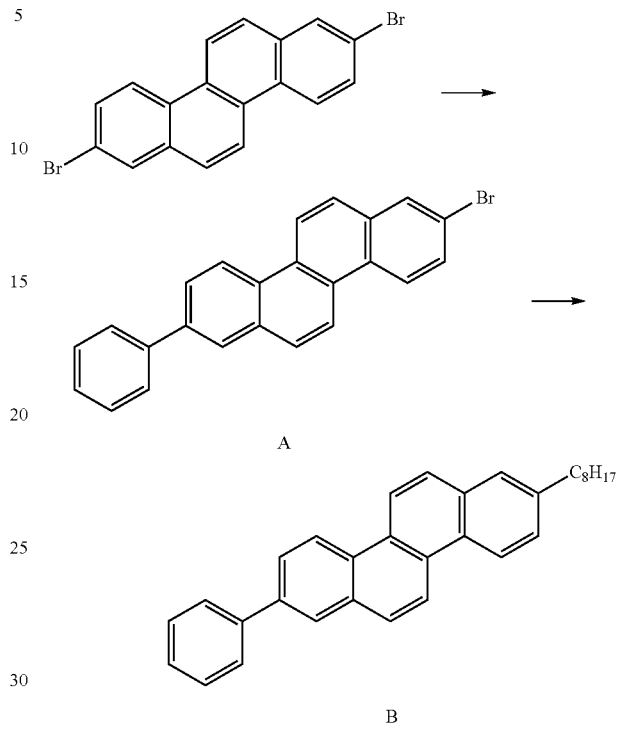

Figure 1:
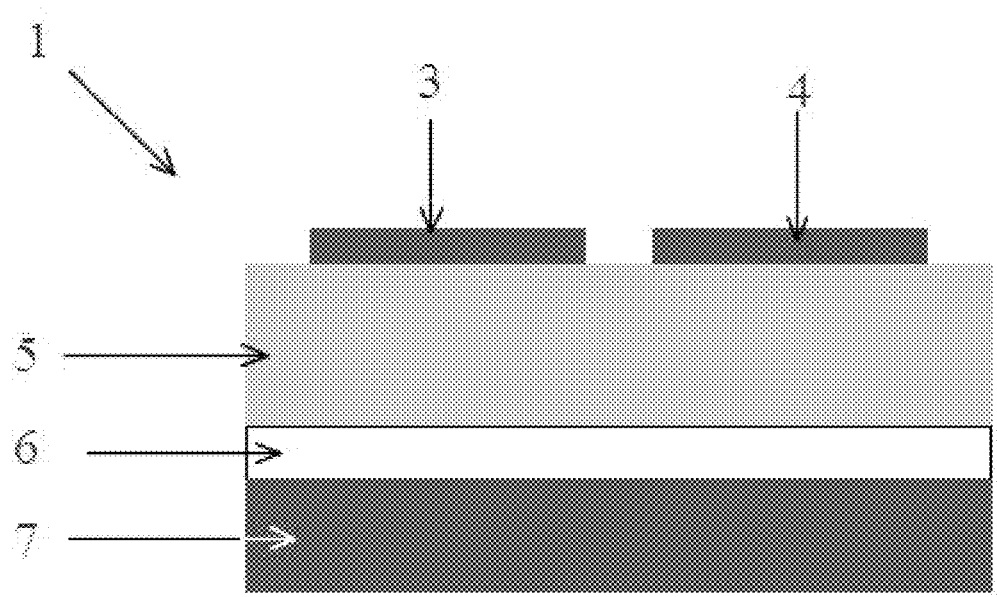
FIG. 1 is a schematic diagram of a top contact FET.
Figure 2:
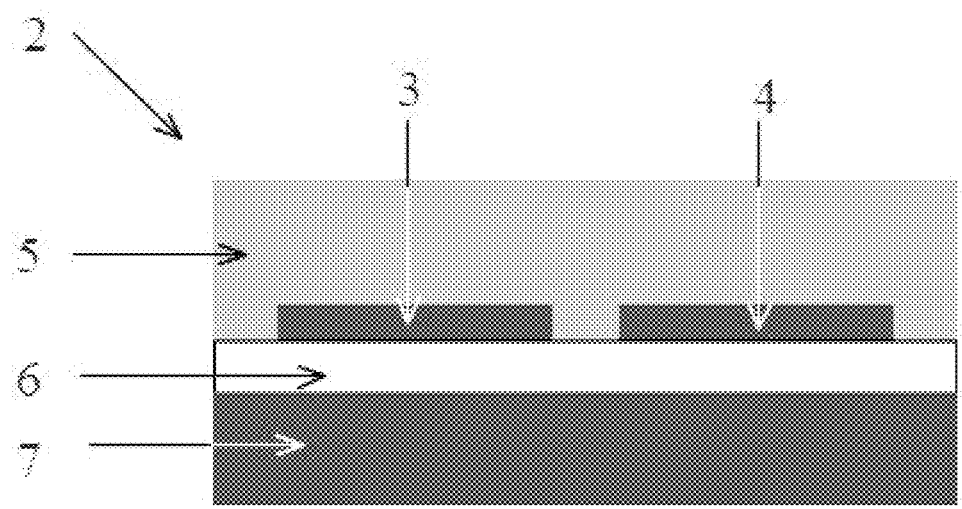
FIG. 2 is a schematic diagram of a bottom contact FET.
Figure 4:
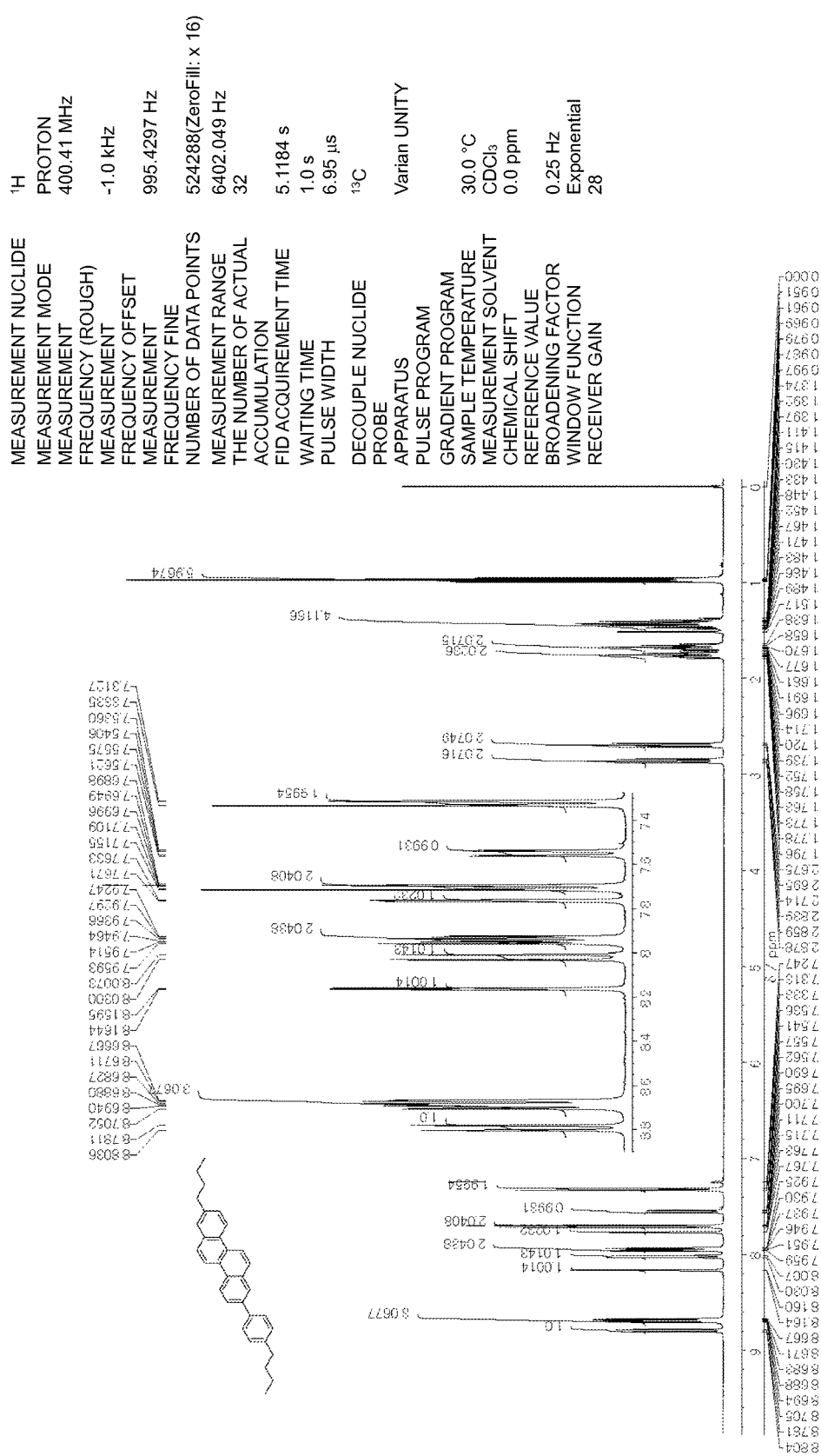
FIG. 4 is a 1H-NMR spectrum diagram of 2-butyl-8-(4-butylphenyl) chrysene (compound D).

Under a nitrogen atmosphere, in a 30 mL three-neck flask with a cooling pipe, after adding 0.089 g (3.13 mmol) of metal magnesium and 2 mL of tetrahydrofuran, 0.55 g (2.87 mmol) of 1-bromooctane was dropped, the mixture was stirred at room temperature for 1 hour, and a Grignard reagent was prepared thereby. Next, under a nitrogen atmosphere, in a 30 mL three-neck flask, 1.0 g (2.61 mmol) of the compound A, 14 mg (0.03 mmol) of [1,3-bis(diphenylphosphino)propane]dichloronickel (II), and 15 mL of tetrahydrofuran were added, and the mixture was cooled to 0° C. Subsequently, the Grignard reagent of 1-bromooctane that was prepared in advance was added, and the mixture was stirred at 0° C. for 4 hours. After the end of the reaction, dilute hydrochloric acid and heptane were added and crystal was filtrated. The resulted crude product was purified by the column chromatography and recrystallization, and a compound B was obtained thereby. A 1H-NMR spectrum of the compound B is shown in FIG. 4.

Synthesis (Manufacture) Method of 2-butyl-8-(4-butylphenyl) chrysene (Compound D: Hereinafter, referred to as 4P-28CR-4)

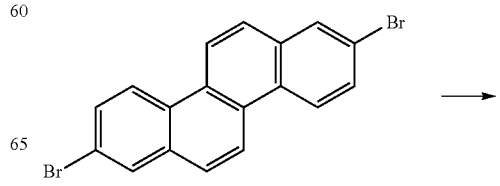

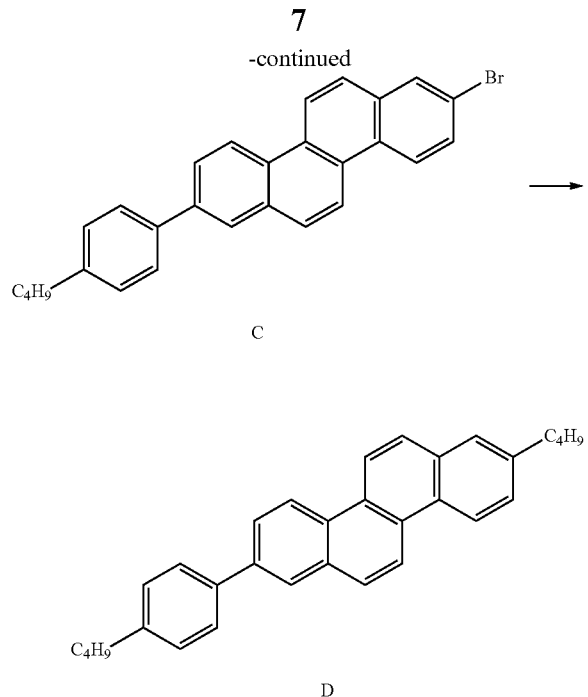

The 2,8-dibromochrysene that is a starting material is the same as described above.

Synthesis of Compound C

Under a nitrogen atmosphere, in a 30 mL three-neck flask with a cooling pipe, 1.0 g (2.59 mmol) of 2,8-dibromochrysene, 0.42 g (2.33 mmol) of p-(n-butyl)phenyl boronic acid, 30 mg (0.03 mmol) of tetrakistriphenylphosphine palladium, 0.49 g (4.66 mmol) of sodium carbonate, 15 ml of toluene, and 4 ml of water were added and the mixture was stirred at 80° C. for 16 hours. After the end of reaction, the mixture was cooled to room temperature, heptane and water were added and crystal was filtrated. The resulted crude product was purified by column chromatography and recrystallization, and a compound C was obtained.

Synthesis of Compound D

Under a nitrogen atmosphere, in a 30 mL three-neck flask with a cooling pipe, after adding 0.079 g (2.28 mmol) of metal magnesium and 2 mL of tetrahydrofuran, 0.34 g (2.50 mmol) of 1-bromobutane was dropped, the mixture was stirred at room temperature for 1 hour, and a Grignard reagent was prepared. Next, under a nitrogen atmosphere, in a 30 mL three-neck flask, 1.0 g (2.28 mmol) of the compound A, 12 mg (0.02 mmol) of [1,3-bis(diphenylphosphino)propane]dichloronickel (II), and 15 mL of tetrahydrofuran were added, and the mixture was cooled to 0° C. Subsequently, the Grignard reagent of 1-bromobutane that was prepared in advance was added, and the mixture was stirred at 0° C. for 4 hours. After the end of the reaction, dilute hydrochloric acid and heptane were added and crystal was filtrated. The resulted crude product was purified by the column chromatography and recrystallization, and a compound D was obtained thereby. A 1H-NMR spectrum of the compound D is shown in FIG. 5.

Example 2

In order to investigate the transistor performance, the respective elements were prepared as shown below.

Preparation of Single Crystal Transistor (Casting Method)

A silicon wafer on which a thermal oxide film having a thickness of 210 nm was formed (Si/SiO$_2$ (bare)) and a silicon wafer on which a polymethyl methacrylate (PMMA) insulating film (film thickness: 30 nm) was prepared by coating a toluene solution (0.7% by weight) of PMMA according to a spin coat method (number of rotation: 2000 rpm, 30 seconds), and subsequently by heat treating at 120° C. for 4 hours were used as substrates.

On these substrates, a mesitylene solution of the compound B (0.08% by weight) was cast under air, and a single crystal was prepared on the substrates.

At both ends of the single crystal, after a carbon paste was coated and molded as a drain electrode, top contact type FET elements were prepared, and under reduced pressure, FET measurement was performed. In the same manner, single crystal transistor elements of the compound D were prepared.

Preparation of Organic Thin Film Transistor (Coating: Spin Coat)

A thin film was prepared by spin coating (number of rotation: 2000 rpm, 30 seconds) a toluene solution of the compound B (0.4% by weight) on a substrate of the bottom contact type (d=210 nm, L=10 μm, w=20 cm), and the FET measurement was performed under reduced pressure condition. According to the similar method, a thin film transistor element was prepared according to the spin coat method of the compound D.

Preparation (Vapor Deposition) of Organic Thin Film Transistor

The compound B was deposited on the substrate at a thickness of 50 nm using a vacuum deposition apparatus, further thereon, gold that becomes a source, drain electrode was deposited at a thickness of 80 nm (L=50 μm, W=1.5 mm) by an electron beam method, and a top contact type element was prepared thereby, and under reduced pressure condition, the FET measurement was performed. As the substrate, the silicon wafer (Si/SiO$_2$) substrates that were respectively surface treated with polystyrene (PS) and CYTOP and a non-treated (bare) substrate were used, and organic films were prepared at room temperature, 60 and 100° C. It was found by the AFM measurement that a film thickness of the PS was 13 nm, and a film thickness of the CYTOP was 27.8 nm. In the same method, thin film transistor elements of the compound D were prepared. Here, the CYTOP is a fluororesin having an amorphous structure and transparency and is used for a coating material, an insulating film and the like.

Results of measurement of performance of the respective elements prepared as described above are shown in Table 1.

TABLE 1

Results of measurement

| Compound | FILM DEPOSITION METHOD | INSULATING FILM | MOBILITY $\mu_{FET}$ [cm$^2$V$^{-1}$s$^{-1}$] | $I_{on}/I_{off}$ | $V_{th}$ [V] |
|---|---|---|---|---|---|
| 4P-28CR-4 | CAST METHOD (SINGLE CRYSTAL) | bare (S$_i$O$_2$) | 0.6 | 10$^3$ | −30 |
| Compound D | CAST METHOD (SINGLE CRYSTAL) | PMMA | <u>2.7</u> | 10$^2$ | −23 |
| | COATING/SPIN COAT METHOD | bare | 4.6 × 10$^{-4}$ | 10$^4$ | −39 |
| | VACUUM DEPOSITION METHOD/ ROOM TEMPERATURE | bare | 2.7 × 10$^{-3}$ | 10$^3$ | −67 |
| | VACUUM DEPOSITION METHOD/ ROOM TEMPERATURE | PS | 4.3 × 10$^{-3}$ | 10$^3$ | −33 |
| | VACUUM DEPOSITION METHOD/ ROOM TEMPERATURE | SYTOP | 2.8 × 10$^{-2}$ | 10$^4$ | −48 |
| | VACUUM DEPOSITION METHOD/60° C. | bare | 5.8 × 10$^{-3}$ | 10$^2$ | −61 |
| | VACUUM DEPOSITION METHOD/60° C. | PS | 1.8 × 10$^{-2}$ | 10$^3$ | −36 |
| | VACUUM DEPOSITION METHOD/60° C. | CYTOP | <u>0.2</u> | 10$^5$ | −51 |
| | VACUUM DEPOSITION METHOD/100° C. | bare | 5.0 × 10$^{-3}$ | 10 | −41 |
| | VACUUM DEPOSITION METHOD/100° C. | PS | 5.2 × 10$^{-2}$ | 10$^2$ | −40 |
| | VACUUM DEPOSITION METHOD/100° C. | CYTOP | 9.4 × 10$^{-2}$ | 10$^3$ | −48 |
| P-28CR-8 | CAST METHOD (SINGLE CRYSTAL) | PMMA | <u>2.0</u> | 10$^4$ | −21 |
| Compound B | COATING/SPIN COAT METHOD | bare | 1.5 × 10$^{-4}$ | 10$^3$ | −41 |
| | VACUUM DEPOSITION METHOD/ ROOM TEMPERATURE | bare | 9.5 × 10$^{-3}$ | 10$^4$ | −54 |
| | VACUUM DEPOSITION METHOD/ ROOM TEMPERATURE | PS | 0.1 | 10$^4$ | −24 |
| | VACUUM DEPOSITION METHOD/ ROOM TEMPERATURE | SYTOP | 0.5 | 10$^4$ | −43 |
| | VACUUM DEPOSITION METHOD/60 | bare | 5.9 × 10$^{-2}$ | 10$^5$ | −40 |
| | VACUUM DEPOSITION METHOD/60 | PS | 3.9 × 10$^{-2}$ | 10$^4$ | −29 |
| | VACUUM DEPOSITION METHOD/60 | CYTOP | <u>2.2</u> | 10$^5$ | −65 |
| | VACUUM DEPOSITION METHOD/100 | bare | 0.1 | 10$^3$ | −80 |
| | VACUUM DEPOSITION METHOD/100 | PS | 0.4 | 10$^4$ | −56 |
| | VACUUM DEPOSITION METHOD/100 | CYTOP | <u>3.1</u> | 10$^4$ | −57 |

Numerical values particularly excellent in the mobility are shown with an underline.

INDUSTRIAL APPLICABILITY

The invention according to the present application shows particular transistor performance as shown above and can be expected to be widely used as the organic semiconductor material.

EXPLANATION OF REFERENCE NUMERALS

1: TOP CONTACT TYPE FET
2: BOTTOM CONTACT TYPE FET
3: SOURCE
4: DRAIN
5: ORGANIC SEMICONDUCTOR
6: INSULATING FILM
7: SUBSTRATE (GATE)

What is claimed is:

1. An organic semiconductor material comprising a chrysene skeleton shown by the following chemical formula CF1:

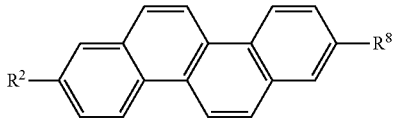

wherein R$^2$ and R$^8$ each is neither a hydrogen atom nor the same functional group, and independently represents an alkyl group having 1 to 30 carbon atoms, an aryl group having 5 to 60 carbon atoms, or a heterocyclic group having 3 to 60 carbon atoms, and wherein each of said groups may have a substituent group,
wherein R$^2$ and R$^8$ are asymmetric on the chrysene skeleton.

2. The organic semiconductor material according to claim 1, wherein said chrysene skeleton has a chrysene skeleton shown by the following chemical formula CF2:

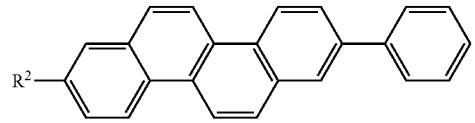

wherein R$^2$ represents an alkyl group having 1 to 30 carbon atoms, or an aryl group having 5 to 60 carbon atoms excluding a nonsubstituted phenyl group, and wherein said each of said groups may have a substituent group.

3. The organic semiconductor material according to claim 1, wherein said chrysene skeleton has a chrysene skeleton shown by the following chemical formula CF3:

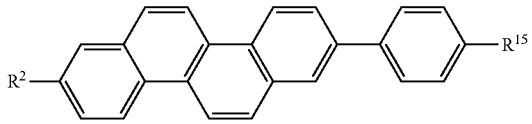

wherein R$^2$ and R$^{15}$ each independently represents an alkyl group having 1 to 30 carbon atoms, and wherein said alkyl group may have a substituent group.

4. An organic semiconductor device comprising the organic semiconductor material according to claim 1.

5. An organic semiconductor device comprising the organic semiconductor material according to claim 2.

6. An organic semiconductor device comprising the organic semiconductor material according to claim 3.

7. An organic electronic device comprising the organic semiconductor material according to claim 1 in a combination with a plurality of additional organic semiconductor materials.

8. An organic electronic device comprising the organic semiconductor material according to claim 2 in a combination with a plurality of additional organic semiconductor materials.

9. An organic electronic device comprising the organic semiconductor material according to claim 3 in a combination with a plurality of additional organic semiconductor materials.

10. An organic semiconductor material comprising a chrysene skeleton shown by the following chemical formula CF2:

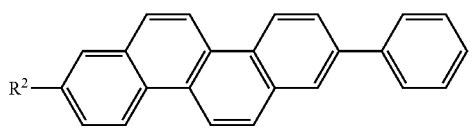

wherein $R^2$ represents an alkyl group having 1 to 30 carbon atoms, wherein $R^2$ is asymmetric on the chrysene skeleton.

* * * * *